Figure 1:
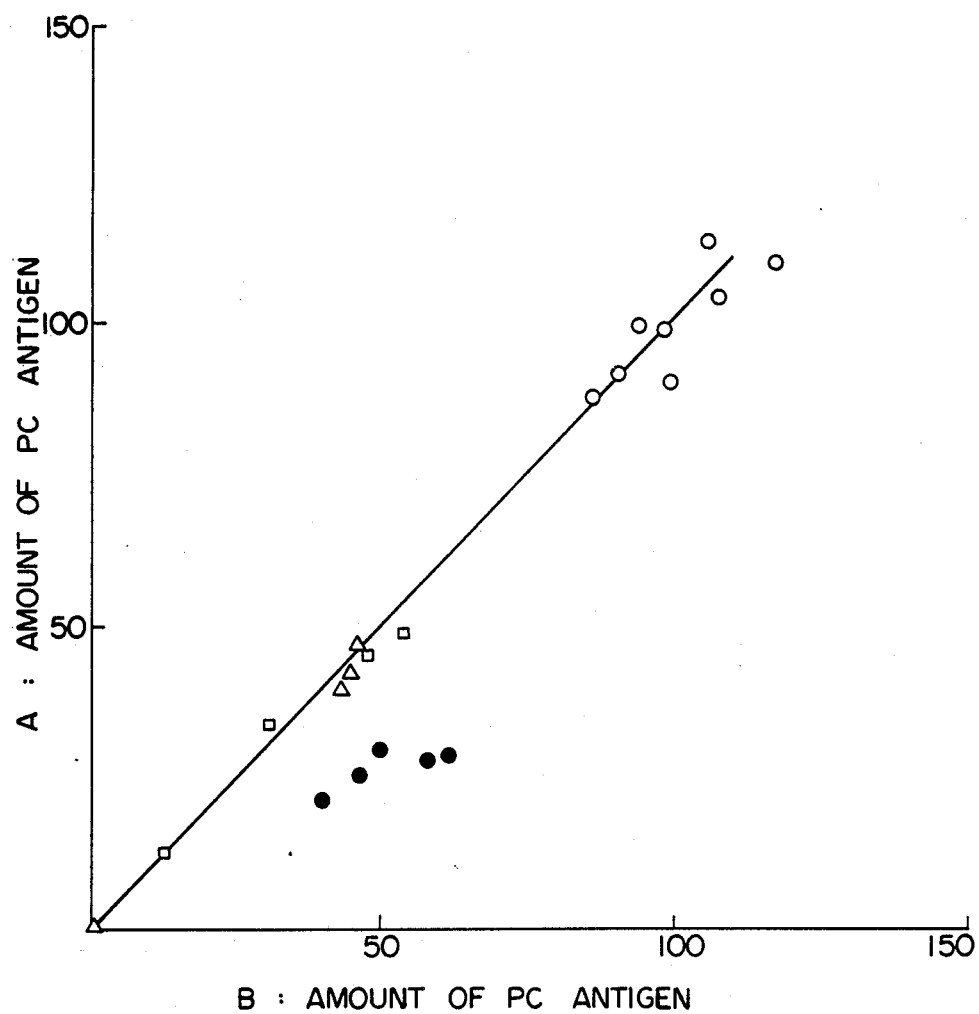

United States Patent [19]

Wakabayashi et al.

[11] Patent Number: 4,902,614

[45] Date of Patent: Feb. 20, 1990

[54] MONOCLONAL ANTIBODY TO HUMAN PROTEIN C

[75] Inventors: Kenji Wakabayashi; Yoshihiko Sumi, both of Hino; Yataro Ichikawa, Tokorozawa; Yoichi Sakata, Oyama; Jun Mimuro, Utsunomiya; Nobuo Aoki, Tokyo, all of Japan

[73] Assignee: Teijin Limited, Osaka, Japan

[21] Appl. No.: 804,255

[22] Filed: Dec. 3, 1985

[30] Foreign Application Priority Data

Dec. 3, 1984 [JP] Japan ................................ 59-254186
Jun. 10, 1985 [JP] Japan ................................ 60-124388

[51] Int. Cl.$^4$ .................. G01N 33/53; G01N 33/577; C07K 1/14; C12N 1/00
[52] U.S. Cl. ...................................... 435/7; 435/172.2; 435/240.27; 435/815; 436/501; 436/548; 530/381; 530/387; 530/413; 935/110
[58] Field of Search ............ 435/7, 13, 240.27, 172.2, 435/212, 219, 226, 815; 436/517, 514, 515, 548, 518, 501; 530/353, 381, 380, 346, 387, 413; 935/106, 108, 110

[56] References Cited

U.S. PATENT DOCUMENTS

| 4,343,734 | 8/1982 | Lian et al. | 530/412 |
| 4,444,744 | 4/1984 | Goldenberg | 424/1.1 |
| 4,486,530 | 12/1984 | David et al. | 436/523 |
| 4,696,895 | 9/1987 | Yamashita et al. | 435/7 |

FOREIGN PATENT DOCUMENTS

0138222 9/1984 European Pat. Off.
0118256 4/1985 European Pat. Off.
8501941 5/1985 PCT Int'l Appl.

OTHER PUBLICATIONS

Kohler et al., Nature, vol. 256, Aug. 7, 1975, pp. 495–497.
Suzuki et al., Chemical Abstract, No. 53016v, 1984, Blood & Vessel, vol. 15(2), pp. 171–174.
Esmon et al., The Journal of Biological Chemistry, vol. 258, No. 9, 1983, pp. 5548–5553.
Johnson et al., The Journal of Biological Chemistry, vol. 258, No. 9, 1983, pp. 5548–5553.
Sugo et al., The Journal of Biological Chemistry, vol. 259, No. 9, 1984, pp. 5705–5710.
Laurell et al., "Chemical Abstracts", 103(25) Col. 213021 q (1985), Febs Letters, vol. 191 (1), pp. 75–81, 1985.
Suzuki et al., "Chemical Abstracts", 101(7) col. 53016v (1984), J. Biochem., vol. 97, pp. 127–138, 1985.

*Primary Examiner*—Esther M. Kepplinger
*Assistant Examiner*—Florina B. Hoffer
*Attorney, Agent, or Firm*—Wenderoth, Lind & Ponack

[57] ABSTRACT

A monoclonal antibody which is specific to human protein C which has calcium bound at the gammacarboxyglutamic acid(Gla) domain and does not recognize human protein C which is not bound to calcium at the Gla domain. The monoclonal antibody is used in an immunoassay method for determining human protein C having a Gla domain and in a method for recovering human protein C having a Gla domain.

4 Claims, 1 Drawing Sheet

MONOCLONAL ANTIBODY TO HUMAN PROTEIN C

This invention relates to a monoclonal antibody to human protein C, a hybridoma which produces the monoclonal antibody, a method of producing the monoclonal antibody from the hybridoma, and to a method of determining or separating human protein C by utilizing an antigenantibody reaction between the monoclonal antibody and protein C.

Protein C which has recently aroused interest as a control factor on coagulation and fibrinolytic systems is a vitamin K-dependent plasma protein, one of gamma-carboxyglutamic acid (Gla)-containing proteins, and is known to show strong anticoagulating activity and fibrinolysis promoting activity see Kisiel, et al., Biochemistry, 16, 5824–5831 (1977); and P. C. Comp & C. T. Esmon: J. Clin. Invest., 68, 1221–1228 (1977)].

Human protein C is produced in the liver. It is the product of gamma-carboxylation of glutamic acid (Glu) existing in the vicinity of the amino terminal of a human protein C precursor formed in the liver to Gla (gamma-carboxylglutamic acid) in the presence of vitamin K. The resulting human protein C is thereafter secreted in the blood. In the blood, most of it exists as a two-chain structure composed of an L-chain having a molecular weight of 21,000 and an H-chain having a molecular weight of 41,000, and has a Gla domain containing 9 Gla residues at the L-chain amino terminal.

It is known that the Gla domain has a calcium binding site, and when a calcium ion ($Ca^{++}$) binds to this site, the protein C undergoes conformational change, and this change is important in the manifestation of activity in vivo [see N. L. Esmon et al.: J. Bil. Chem., 258, 5548–5553 (1983)].

When vitamin K is deficient or an antagonist of vitamin K (warfain, discoumarol, etc.) is administered, the gamma-carboxylation of the human protein C precursor does not proceed. In this case, Glu in the vicinity of the amino terminal of the human protein C precursor is not converted to Gla, but secreted in the blood. Such a protein secreted in the blood which has the same structure as the human protein C precursor will be abbreviated as PIVKA-PC which means protein C as protein induced by vitamin K absence or antagonists. Since PIVKA-PC does not have a completed Gla domain as in protein C, it does not completely undergo Gla-dependent change in steric structure even in the presence of a calcium ion ($Ca^{++}$), and is not biologically active. For this reason, PIVKA-PC is treated as an abnormal protein in a living organism. No method has previously been available for measuring or determining PIVKA-PC and protein C having a Gla domain discriminatingly by using a monoclonal antibody.

Since human protein C has a short half life in a living organism, the effects of the absence of vitamin K and the administration of a vitamin K antagonist tend to appear early. Furthermore, unlike other gla-containing coagulating factors (prothrombin, FVII, FIV and FX) which act on the proceeding of coagulation, protein C has the action of inhibiting coagulation. Hence, to determine PIVKA-PC and normal protein C discriminatingly becomes a very useful parameter in determining the state of absence or deficiency of vitamin K or effects of administering a vitamin K antagonist (such as warfarin and dicumarol).

On the other hand, a monoclonal antibody has recently gained widespread acceptance in analysing the function and structure of an antigen protein or in immunoassay such as enzyme immunoassay (E.I.A.) or radioimmunoassay (RIA) because it has the advantage that it is specific to a single antigen determinant and antibodies having the same specificity can be stably produced. For the functional analysis and molecular analysis of an antigen protein, it will be an effective means to find out an antibody which recognizes a site involved in the function of the antigen protein, or a special structural site.

Monoclonal antibodies to human protein C as an antigen protein have been proposed (Blood & Vessel, 1984, vol. 15, NO. 2, pages 171–174; J. Biochem., vol. 97, No. 1, 1985, pages 127–138; and Japanese Laid-Open Pat. Publication No. 120,825/1985). These documents disclose 13 monoclonal anntibodies to human protein C in total. Six out of these bind to the L-chain of protein C; five, to the H-chain of protein C; and two recognize an area between the L-chain and H-chain of protein C. J. Biochem., vol. 97, No. 1, 1985, pages 127–138 states at the end: "Of the present antibodies produced, some might be conformation-specific antibodies directed toward the metal ion-dependent structure of the protein". This, however, is a speculation, and this paper does not describe the fact that such conformation-specific antibodies were actually obtained. Such a fact has neither been reported subsequently.

In addition, the binding sites of the above 13 monoclonal antibodies to human protein C are sites common to protein C and PIVKA-PC. Accordingly, by these monoclonal antibodies, protein C and PIVKA-PC cannot be measured or determined distinguishably.

It is an object of this invention therefore to provide a novel monoclonal antibody to human protein C.

Another object of this invention is to provide a monoclonal anibody to human protein C which specifically recognizes human protein C in the Gla domain.

Another object of this invention is to provide a monoclonal antibody to human protein C which specifically recognizes human protein C in the Gla domain which has undergone change in conformation by a calcium ion.

Another object of this invention is to provide a monoclonal antibody to human protein C which can distinguishably recognize protein C and PIVKA-PC having no completed Gla domain as in protein C.

Another object of this invention is to provide a hybridoma which produces the aforesaid monoclonal antibody of the invention.

Another object of this invention is to provide a method of separating and recovering the monoclonal antibody from the product of the aforesaid hybridoma.

Another object of this invention is to provide a method of determining human protein C which comprises determining the content of human protein C in a mixture containing human protein C through an antigen-antibody reaction using the monoclonal antibody of the invention.

Another object of this invention is to provide a method of capturing human protein C by contacting a mixture containing the human protein C with the monoclonal antibody of the invention fixed to an insoluble carrier by utilizing the property of the monoclonal antibody of the invention to recognize specifically human protein C binding the calcium ion.

Further objects and advantages of this invention will become apparent from the following description.

According to this invention, the above objects and advantages of this invention are achieved firstly by a monoclonal antibody to human protein C which does not recognize human protein C not binding a calcium ion at the Gla domain but recognizes human protein C binding a calcium in at the Gla domain.

According to this invention, the monoclonal antibody to human protein C in accordance with this invention can be produced by separating and recovering a monoclonal antibody to human protein C from the product of a hybridoma capable of producing a monoclonal antibody to human protein C which does not recognize human protein C not binding a calcium ion at the Gla domain but recognizes human protein C binding a calcium ion at the Gla domain.

The present invention also provides the aforesaid hybridoma and a process for producing a monoclonal antibody using the hybridoma.

The hybridoma cells capable of producing the monoclonal antibody of this invention can be obtained by a method known as the Köler-Milstein method Köhler & Milstein: Nature, 256, 495–497 (1975)]. Specifically, mice are immunized with human protein C, and the spleen cells are extracted from the immunized mice. The spleen cells are then fused with mouse myeloma cells. The resulting hybridoma cells are systematically examined and screened against an antibody reacting with human protein C fixed to microtiter plates. The examination is carried out both in the presence of a calcium ion ($Ca^{++}$) and in the absence of a calcium ion. By selecting those hybridoma cells which prove to be positive only in the former reaction in the presence of a calcium ion are selected, and isolated. These hybridoma cells synthesize an secrete the desired antibody.

The monoclonal antibody of this invention is obtained from a product produced by these novel hybridoma cells, and acts monospecifically on a specific antigen determinant on the human protein C molecule in the presence of a calcium ion.

A specific process for producing the monoclonal antibody in this invention will now be described in detail.

A. Isolation And Purification Of An Antigen

Human protein C used as an antigen is isolated from a human plasma and purified by the method of Suzuki et al., J. Biol. Chem., 258, 1914–1920 (1983)].

B. Immunization Of A Mouse With Human Protein C

Female Balb/C mice may be used, but mice of other strains may also be used. The immunizing plan and the concentration of human protein C should be selected so as to form a sufficient amount of antigenically stimulated lymphocytes. For example, a mouse is immunized intraperitoneally with 50 micrograms of human protein C three times at 2-week intervals, and finally 30 micrograms of human protein C is administered intravenously. Several days after the final immunization, the spleen cells are extracted from the animal for fusion.

C. Cell Fusion

The spleen was aseptically taken out from the immunized mouse, and a suspension of the spleen cells was prepared. The spleen cells are fused with mouse myeloma cells from a suitable cell line in the presence of a suitable fusion promotor The preferred ratio of the spleen cells to the myeloma cells is from about 20:1 to about 2:1, and a fusion medium is suitably used in an amount of 0.5 to 1.5 ml per about $10^8$ spleen cells.

The mouse myeloma cells used for cell fusion are well known. In the present invention P3-X63-Ag 8-U1 cells (P3-U1) see D. E. Yelton et al., Current Topics in Microbiology and Immunology, 81, 1 (L978)]are used.

The fusion promoter is preferably polyethylene glycol having an average molecular weight of 1000 to 4000. Other fusion promoters known in the art can also be used. In the present invention, polyethylene glycol having an average molecular weight of 1540 is preferably used.

D. Screening Of The Fused Cells

In a separate container (such as a microtiter plate), a mixture composed of the unfused spleen cells, unfused mouse myeloma cells and the fused hybridoma cells are diluted with a selective medium not supporting the unfused mouse myeloma cells, and cultured for a period sufficient to kill the unfused mouse myeloma cells (about 1 week). A culture medium having drug resistance (for example, resistance to 8-azaguanine) and not supporting the unfused mouse myeloma cells, such as HAT medium, is used. In the selective medium, the unfused myeloma cells die. Since the unfused spleen cells are untransformed cells, they die away after a certain period of time (1 week). The fused cells, on the other hand, can survive in the selective medium since they have both the tumoral nature of the parent cells of myeloma and the nature of the parent spleen cells.

E. Determination Of Human Protein C

After the hybridoma cells have thus been detected, the culture supernatant is sampled and screened for an antibody to human protein C by enzyme linked immunosorbent assay (ELISA). The assay is carried out by adding $CaCl_2$ in a certain concentration to the culture supernatant, an enzyme-labelled antibody solution and a washing solution, and also in the absence of $CaCl_2$ By selecting those hybridomas which prove to be positive only in the presence of $CaCl_2$ are selected. These hybridomas produce and secrete an antibody which does not recognize human protein C in the absence of a calcium ion but recognizes human protein C in the presence of a calcium ion.

F. Cloning Of The Hybridoma Cells Producing The Desired Antibody And The Production Of The Antibody The hybridoma cells capable of producing the desired antibody are cloned by a suitable method such as a limiting dilution method, and the desired antibody can be produced by the following two different methods. According to a first method, the hybridoma cells are cultured in a suitable medium for a certain period of time, and the monoclonal antibody produced by the hybridoma cells can be isolated from the supernatant of the culture. According to a second method, the hybridoma cells are injected intraperidoneally into a syngenic mouse. After a certain period of time, the monoclonal antibody produced by the hybridoma cells can be isolated from the blood and ascites of the host animal.

G. Separation Of Human Protein From The Human Protein C-Containing Mixture

The monoclonal antibody of this invention, as stated above, has ,the property of not recognizing human protein C in the absence of a calcium ion ($Ca^{++}$) but specifically recognizing human protein C in the presence of a calcium ion ($Ca^{++}$). By utilizing this property, human protein C can be easily separated from a mixture containing human protein c (for example human plasma).

For this purpose, the monoclonal antibody to human protein C is first fixed or bound to an insoluble carrier. The insoluble carrier used at this time may be any of those which are generally used as substrates for assay reagents or kits based on the use of monoclonal antibodies. For example, the insoluble carrier may be produced from such a material as Sepharose, polyacrylamide, cellulose, dextran, a maleic acid polymer or mixtures of these. The insoluble carrier may be in various forms such as a powder, granules, pellets, beads, a film or a fiber. Generally, it is advantageous to use plates having many depressions (wells) used for assaying or separating plasma or its fractionated components.

When the fixed monoclonal antibody is brought into contact with a mixture containing human protein C in the presence of a calcium ion ($Ca^{++}$), human protein C is bound to the fixed monoclonal antibody and thus captured.

As required, the human protein C captured by the fixed monoclonal anibody is separated by washing it with an aqueous solution containing a calcium ion together with the carrier to which it is fixed to thereby remove the remainder of the mixture, and then treating the fixed monoclonal antibody with an aqueous medium substantially free from a calcium ion.

Thus, the separating method in accordance with this invention permits removal of human protein C from a mixture containing human protein C, separation of human protein from the mixture and its purification, and measurement of the content of human protein C in the mixture by very simple operations. For example, the content of human protein C having a Gla domain in a mixture containing it can be determined by using the monoclonal antibody to human protein C in accordance with this invention, and inducing an antigen-antibody reaction between them, preferably in the presence of a calcium ion. Furthermore, the amount of Gla-deficient protein C (PIVKA-PC) may be determined by combining the content of human protein C determined by the above method with the results of measurement of the amount of entire protein C by an immunological technique (such as the EIA, RIA or the Laurell method) using a monoclonal antibody, which recognizes a site having no relation to a Gla-dependent steric structural change (a polyclonal antibody or an antiserum).

The following Examples illustrate the present invention more specifically. In these Examples, protein C will sometimes be abbreviated as PC.

EXAMPLE 1

Two female Balb/C mice (4 weeks old) were immunized with purified human PC four times at 14-day intervals. The first immunization was effected by intraperitoneally administering to the mice a mixture (emulsion) of 50 micrograms of human PC dissolved in phosphate buffer saline (PBS) and an equal volume of complete Freund's adjuvant in an amount of 0.5 ml/head. The second and third immunizations were effected by intraperitoneally administering to the mice a mixture of 50 micrograms of human PC and Freund's incomplete adjuvant. The final immunization was carried out by administering a BPS solution of 30 micrograms of human PC from the tail veins of the mice. Three days after the final immunization, the spleen cells of the immunized mice were used for cell fusion.

The spleen cells of the immunized mice and myeloma cells (P3U1) of a mouse of the same strain were mixed in a ratio of from about 2:1 to about 15:1 and fused in the presence of 50% polyethylene glycol 1540 (a product of Wako Pure Chemicals, Co., Ltd.) in accordance with the method of Köhler and Milstein. The fused cells were suspended in RPMI-1640 medium (containing 10% FCS) so that the concentration of the cells became $1 \times 10^6$ cells/ml. The suspension was distributed to the wells of a 96-well microplate (Coster) in an amount of 100 microliters per well.

The fused cells were incubated in a $CO_2$ incubator (5% $CO_2$, 37° C.) After one day, a medium containing hypoxanthine, aminopterin and thymidine (HAT media) was added to each well, and a half volume of the medium in each well was removed and the HAT medium was added to each well every second or third day. Thus, hybridoma cells composed of the spleen cells and the myeloma cells were screened.

The antibody in the supernatant of the culture of the hybridoma cells was detected by the ELISA method using a microtiter plate coated with human PC as an antigen. As a second antibody, an alkaline phoaphatase-labelled rabbit anti-mouse IgG antibody was used, and to determine the difference of the bonding of human PC to the antibody in the presence of calcium ion from that in the absence of calcium ion, TBS (0.02M Tris/HCl, 0.14M NaCl, pH 7.4) containing 5 mM $CACl_2$ was added to one supernatnat from one well, and TBS was added to another supernatant from same well. Furthermore, TBS containing 5mM $CaCl_2$, 0.05% Tween 20/0.02% $NaN_3$, or TBS/0.05% Tween 20/0.02% $NaN_3$ was used as a diluent for the second antibody and a washing buffer.

In 541 wells in total in which the fused cells were plated, the formation of colonies was observed in 523 wells. Out of these, 44 wells were found to be positive in antibody production as shown in Table 1 below. Forty-four wells showed bonding to human PC in the presence of a calcium ion, and 32 wells showed bonding to human PC in the absence of a calcium ion.

These positive wells were cloned twice by the limiting dilution method. The resulting clones were suspended in 90%FCS-10% DMSO and stored in liquid nitrogen.

The monoclonal antibodies produced by the individual clones were proliferated in the abdominal cavities of Balb/C mice. Human PC was isolated from the ascites of the mice and purified by using a protein A-Sepharose 4B column.

TABLE 1

| | |
|---|---|
| Number of wells in which the fusion cells were plated | 541 |
| Number of wells which formed colonies | 523 |
| Number of wells which produced antibodies | 44 |
| Bonding to PC in the presence of $Ca^{++}$ was positive | 44 |
| Bonding to PC in the absence of $Ca^{++}$ was positive | 32 |

EXAMPLE 2

IgGs of the individual clones purified from the mouse ascites were examined for subclasses, the effect on human PC activity, binding activity to the L-chain or H-chain, and binding activity to human PC whose Gla domain was removed by an enzyme treatment using alphachymotrypsin.

The subclasses were determined by the Ouchterlony method using anti-mouse antisera specific to the individual classes.

The effect on human PC activity was determined by mixing IgG and human PC in a mole ratio of 5:1, incubating the mixture overnight at 4° C. activating human PC by a thrombin-thrombomodulin complex, and measuring the human PC activity by measuring the decomposition activity of a synthesis substrate. As the synthesis substrate,

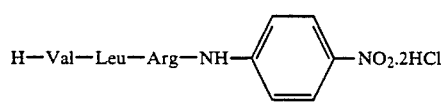

in which val represents optically active D-valine, Leu represents optically active L-leusine, and Arg represents optically active L-arginine; a product of Kabi Vitrum AB of Sweden designated as S-2266).

The binding activity to the L-chain or H-chain was determined by subjecting human PC to electrophoresis under reducing conditions, followed by immunoblotting using a nitrocellulose membrane and HRP-labelled goat anti-mouse IgG.

The Gla domain-removed human PC was prepared by limited hydrolysis using alpha-chymotrypsin in accordance with the method of Esmon et al. [N. L. Esmon et al., J. Bio. Chem., 258, 5548–5553 (1983)], and by immonoblotting, its bondability to the antibody was determined.

The properties of the antibodies produced by the six clones are summarized in Table 2. The calcium ion-dependent antibodies all bound to the L-chain, and even in the presence of a calcium ion did not bind to human PC from which the Gla domain was removed. These antibodies were shown to bind to the calcium ion and recognize only that human PC which underwent conformation change dependent on the Gla domain.

TABLE 2

| Clone | Subclass | Epitope on protein C (L-chain or H-chain | $Ca^{++}$ dependency | Bonding to the Gla domain-removed PC | Effect on PC activation |
|---|---|---|---|---|---|
| 7B12 | IgG$_1$ | L | + | − | − |
| 10E12 | G$_1$ | L | + | − | − |
| 6H2 | G$_1$ | L | + | − | − |
| 6C3 | G$_2$b | H | − | + | − |
| 10H11 | G$_1$ | H | − | + | + |
| 6B10-1 | G$_1$ | − | − | + | − |

EXAMPLE 3

Measurement Of Human PC In Plasma:

PC was assayed by the following two methods of IRMA (immunoradiometric assay) using plasma samples taken from normal healthy persons, plasma samples taken from patients with protein C deficiency, plasma samples taken from patients with liver disease and plasma samples taken from patients administered with warfarin.

Method A

The plasma samples and a standard plasma sample were each diluted with 0.05M Tris-HCl (pH 7.4)/0.15M NaCl (TBS) containing 1% BSA and distributed to the wells of a microtiter plate coated with the antibody (6C3) capable of binding to the H-chain of PC and blocked with 1% BSA. The plate was incubated at 37° C. for 3 hours and the wells were washed with 1% BSA/TBS/0.05% Tween 20. $^{125}$I-labelled calcium-dependent PC antibody (7B12) diluted with 1% BSA/TBS containing 5mM CaCl$_2$ was added. The plate was incubated at 37 C for 3 hours, and the wells were washed with 1% BSA/TBS/0.05% Tween-20 supplemented with 5mM CaCl$_2$. The wells were then counted by a gamma-counter.

Method B

The procedure of method A was repeated except that $^{125}$I-labelled rabbit anti-human PC antibody was used as the $^{125}$-labelled second antibody.

The results of measurements are shown in the accompanying drawing. In the plasma samples taken from the normal healthy persons, the patients with protein C deficiency and the patients with liver disease, the measured values obtained by the methods A and B well agreed with each other, and the correlation coefficient was $\alpha = 0.99$. In the case of the plasma samples from the patients administered with warfarin, the measured values obtained by the method A were lower than those obtained by the method B. This shows that Gla-deficient PC (PIVKA-PC) which did not undergo conformational change dependent on Gla even in the presence of a calcium ion was secreted in the blood. The amount of the Gla-deficient PC (PIVKA-P) can be taken as the difference between the two measured values obtained by the methods A and B.

In the drawing, the circular marks show the measured values of the samples from the normal healthy persons; the square marks, the measured values of the samples from the patients with liver disease; the triangular circles, the measured values of the samples from the patients with protein C deficiency; and the black circular marks, the measured values of the samples from the patients administered with warfarin.

EXAMPLE 4

Measurement Of The Amount Of PC Antigen Before And After Administration Of Warfarin:

Protein C in plasma samples taken before and after the administration of warfarin was measured by the same two methods A and B as in Example 3.

Table 3 show the results of measurements in two cases. In the two cases, the amount of protein C before the administration of warfarin was in the normal range, and the measured values by the two methods A and B well agreed with each other. But after the administration of warfarin, the protein C level evidently decreased. The amount of PC measured by the method A after administration was one-half of that by the method B or less. This shows that the administration of warfarin decreased the amount of protein C secreted in the blood and the Gla-deficient protein C (PIVKA-PC) was secreted.

TABLE 3

| Warfarin therapy | Method A Gla normal PC [μg/ml] (%) | Method B total PC [μg/ml] (%) |
|---|---|---|
| Sample 1 | | |
| before | 4.01 (93.7) | 4.28 (100) |
| after | 0.53 (12.4) | 1.24 (29.0) |
| Sample 2 | | |
| before | 4.78 (108.6) | 4.40 (100) |
| after | 0.77 (17.5) | 1.52 (34.5) |

Amount of PC antigen before and after administration of warfarin

EXAMPLE 5

(1) Fixation of antibody to an insoluble carrier 0.5 g of a dry gel of Sepharose 4B (made by Pharmacia Fine Chemicals) activated with cyanogen bromide was swollen washed with 100 ml of lmM HCl on a G3 glass filter and further washed with a coupling buffer (0.1M NaHCO$_3$ containing 0.5M NaCl, pH 8.3). After the coupling buffer was removed by sucking, the gel was immediately added to 2 ml of a solution of antibody (6H2) in a coupling buffer (3 mg/ml) and suspended. The suspension was shaken gently overnight at 4 °C. The gel was then transferred to 1M ethanolamine-HCl (pH 8.0, 2 ml) and shaken at room temperature for 2 hours to block the remaining active site. After the blocking, the antibody-coupled Sepharose gel was washed alternately with 0.1M acetate buffer (pH 4.0) containing 0.5M NaCl and 0.1M borate buffer (pH 8.0) containing 0.5M NaCl on a glass filter. When the absorbance of the filtrate at 280 nm reached less than 0.01, it was equilibrated with 5 mM CaCl$_2$ and 0.05M Tris-HCl (pH 7.4), and packed into a column. Affinity chromatography was carried out using the anti-human PC monoclonal antibody (6H2)-coupled Sepharose 4B column so prepared.

(2) Adsorption Of Protein C On The Antibody-Coupled Sepharose 4B And Its Elution Eight milliliters of a 1 M BaCl$_2$ solution was added to 100 ml of a human plasma, and the mixture was stirred at 4° C. for 1 hour. The precipitate was collected by centrifugal separation and washed with 0.1 M NaCl containing 5 mM of BACl$_2$ and 5 mM benzamidine and then dissolved in 0.2 M EDTA (pH 7.4) containing 15 ml of 5mM benzamidine to obtain a barium-adsorbed fraction. The barium-adsorbed fraction was dialyzed against 0.05 M Tris-HCl (pH 7.4) containing 1 mM benzamidine, and a CaCl$_2$ solution was added to that the final concentration reached 5 mM. The mixture was charged onto the antibody (6H2)-coupled column equilibrated with 0.05 M Tris-HCl containing 5 mM CaCl$_2$ and 1mM benzamidine. The column was washed with 0.05 M Tris-HCl containing 5 mM CaCl$_2$, 1 mM benzamidine and 1 M NaCl, and eluted with 0.05 M Tris-HCl containing 50 mM EDTA and 1mM benzamidine. A single peak containing PC was obtained. PC in the fraction eluted from the antibody Sepharose 4B was purified to an extent as high as about 52 times that in the barium adsorbed fraction, and the recovery ratio of PC was about 48.2 %.

What is claimed is:

1. A monoclonal antibody which is specific to human protein C which has calcium bound at the gamma-carboxyglutamic acid (Gla) domain and does not recognize human protein C which is not bound to calcium at the Gla domain.

2. A hybridoma, which produces a monoclonal antibody which is specific to human protein C which has calcium bound at the Gla domain and does not recognize human protein C which is not bound to calcium at the Gla domain.

3. A method of measuring human protein C having a gamma-carboxyglutamic acid (Gla) domain, which comprises:

subjecting an aqueous mixture containing said human protein C having a Gla domain, in the presence of a calcium ion, to an antigen-antibody reaction using a monoclonal antibody specific to a complex of human protein C which has calcium bound at the Gla domain, and subjecting the resulting mixture to a measurement of the amount of the antigen-antibody reaction product as a measure of said human protein C.

4. A method of recovering human protein C having a gamma-carboxyglutamic acid (Gla) domain, which comprises:

bringing an aqueous mixture containing human protein C having a Gla domain in the presence of a calcium ion into contact with a fixed monoclonal antibody comprising an insoluble carrier and fixed thereto a monoclonal antibody specific to a complex of human protein C binding calcium at the Gla domain, whereby the human protein C is captured by the fixed monoclonal antibody in the form in which the calcium ion is bound to the Gla domain, separating the captured human protein C from the fixed monoclonal antibody, separating step being carried by contacting the monoclonal antibody capturing the human protein C having the calcuim ion bound to its Gla domain with an aqueous medium substantially free from a calcium ion, whereby the human protein C is separated from the fixed monoclonal antibody in a form not bing the calcium ion in the Gla domain, and recovering the separated human protein C.

* * * * *